United States Patent [19]

Cosgrove et al.

[11] Patent Number: 5,041,130

[45] Date of Patent: Aug. 20, 1991

[54] FLEXIBLE ANNULOPLASTY RING AND HOLDER

[75] Inventors: Delos M. Cosgrove, Hunting Valley, Ohio; Than Nguyen, Huntington Beach, Calif.

[73] Assignee: Baxter International Inc., Deerfield, Ill.

[21] Appl. No.: 444,189

[22] Filed: Nov. 30, 1989

Related U.S. Application Data

[63] Continuation-in-part of Ser. No. 387,909, Jul. 31, 1989.

[51] Int. Cl.⁵ ............................................. A61F 2/24
[52] U.S. Cl. ................................. 623/2; 623/900
[58] Field of Search .................................. 623/2, 900

[56] References Cited

U.S. PATENT DOCUMENTS

| | | | |
|---|---|---|---|
| 3,656,185 | 4/1972 | Carpentier | 623/2 |
| 4,042,979 | 7/1977 | Angell | 623/2 |
| 4,055,861 | 11/1977 | Carpentier et al. | 623/2 |
| 4,164,046 | 7/1979 | Cooley | 623/2 |
| 4,204,283 | 5/1980 | Bellhouse et al. | 623/2 |
| 4,290,151 | 9/1981 | Massana | 623/2 |
| 4,306,319 | 12/1981 | Kaster | 623/2 |
| 4,489,446 | 12/1984 | Reed | 623/2 |
| 4,585,453 | 4/1986 | Martin et al. | 623/2 |
| 4,602,911 | 7/1986 | Ahmadi et al. | 623/2 |
| 4,865,600 | 9/1989 | Carpentier et al. | 623/2 |

FOREIGN PATENT DOCUMENTS

| | | |
|---|---|---|
| 0200419 | 4/1986 | European Pat. Off. . |
| 0242172 | 4/1987 | European Pat. Off. . |
| 87/05489 | 3/1987 | PCT Int'l Appl. . |
| 2083362 | 12/1978 | United Kingdom . |

OTHER PUBLICATIONS

"Clinical and Hemodynamic Performance of a Totally Flexible Prosthetic Ring for Atrioventricular Valve Reconstruction", Duran, Ubago; The Annals of Thoracic Surgery; vol. 22, No. 5; pp. 248-463.

"Conservative Surgery of the Mitral Valve, Annuloplasty on a New Adjustable Ring", Massana, Calbet and Castells; Cardio. Surg., 1980.

Primary Examiner—Randy Citrin Shay
Attorney, Agent, or Firm—Michael C. Schiffer

[57] ABSTRACT

An assembly for holding a substantially flexible lenticular shaped annuloplasty ring in a substantially taut position for suturing about a valve annulus. The assembly includes a portion which is formed with a surface against which the annuloplasty ring is positioned and held in a shape substantially equivalent to at least a portion of the valve annulus. The assembly further includes a mechanism for releasably binding the annuloplasty ring to this surface.

9 Claims, 4 Drawing Sheets

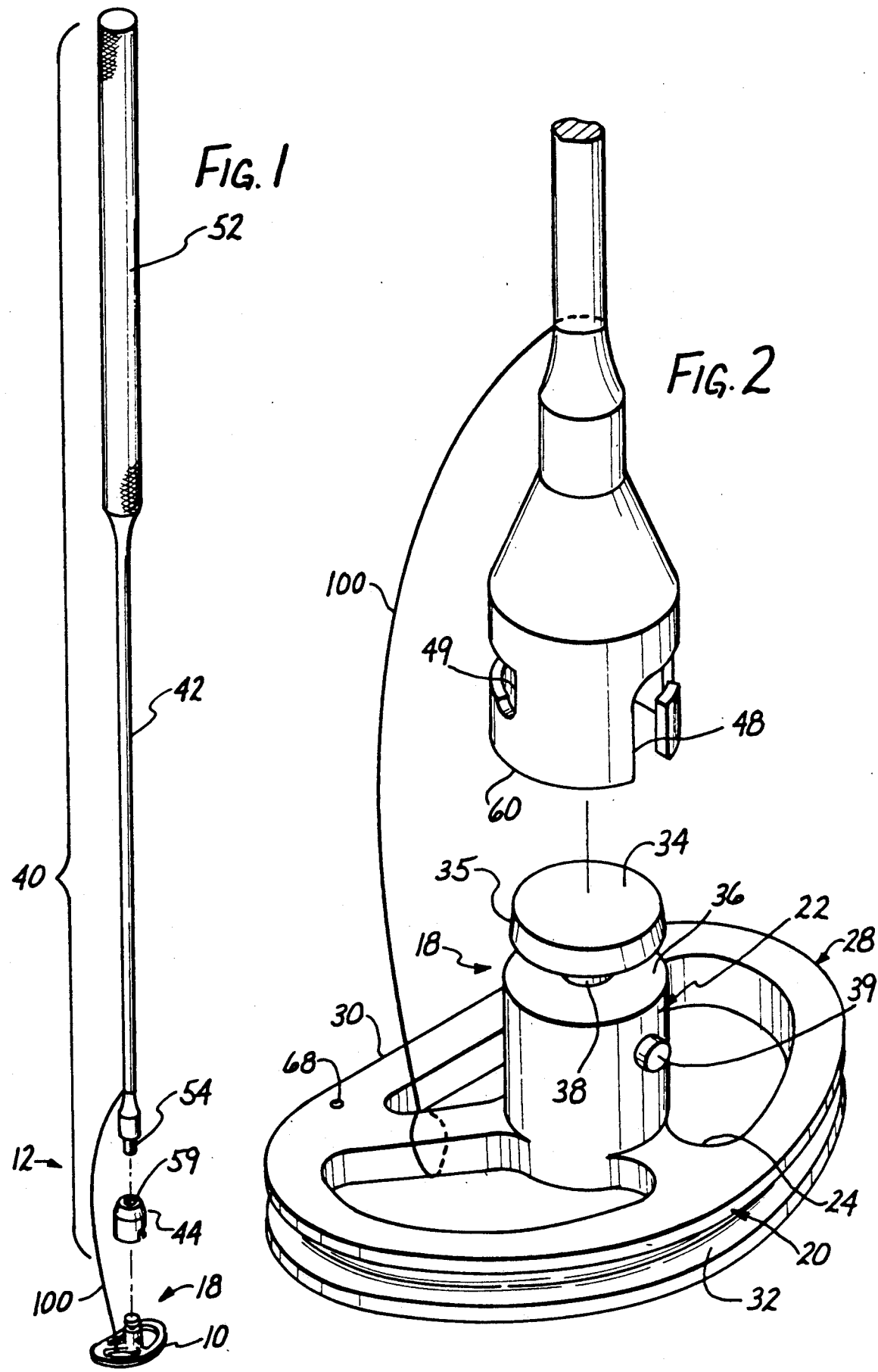

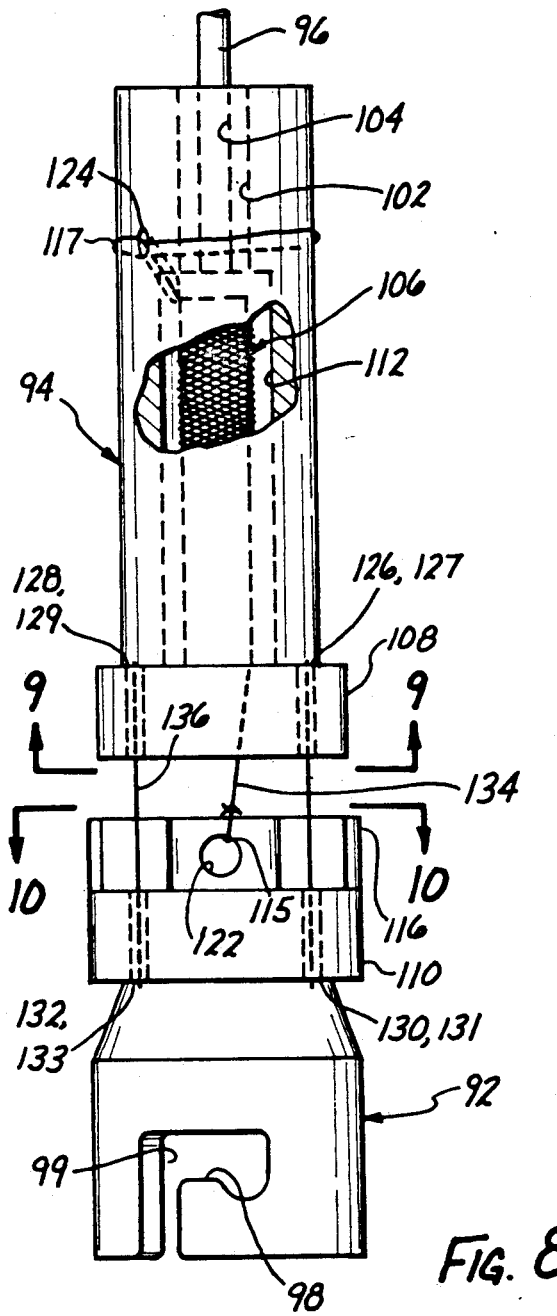
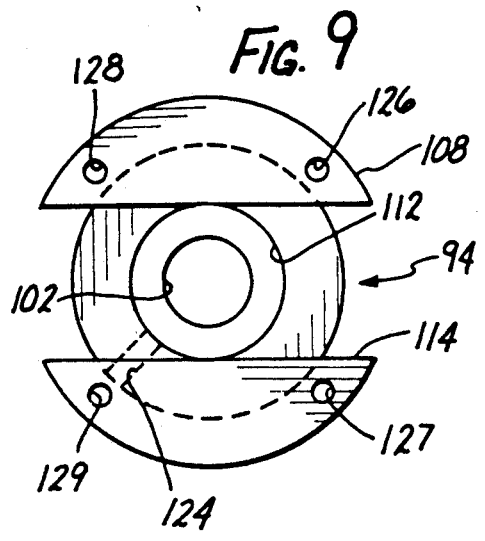
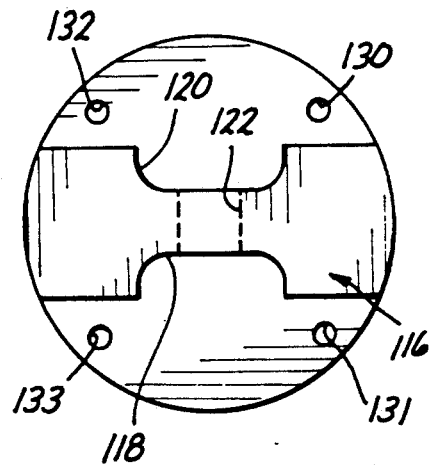
FIG. 8
FIG. 9
FIG. 10

FLEXIBLE ANNULOPLASTY RING AND HOLDER

RELATED APPLICATIONS

This application is a continuation-in-part of co-pending U.S. patent application Ser. No. 387,909, filed on July 31, 1989.

BACKGROUND OF THE INVENTION

The present invention relates to a support for a natural human heart which may be used for the surgical correction of a deformed heart valve, specifically a heart valve which has become dilated. In particular, the present invention relates to a holder and flexible annuloplasty ring prosthesis combination for properly positioning the ring about the valve annulus during implantation.

The human heart generally includes four valves. Of these valves the more critical ones are known as the mitral valve, which is located in the left atrioventricular opening, and the tricuspid valve, which is located in the right atrioventricular opening. Both of these valves are intended to prevent regurgitation of blood from the ventricle into the atrium when the ventricle contracts. In preventing blood regurgitation both valves must be able to withstand considerable back pressure as the ventricle contracts. The valve cusps are anchored to the muscular wall of the heart by delicate but strong fibrous cords in order to support the cusps during ventricular contraction. Furthermore, the geometry of the heart valves ensure that the cusps overlay each other to assist in controlling the regurgitation of the blood during ventricular contraction.

Diseases and certain natural defects to heart valves can impair the functioning of the cusps in preventing regurgitation. For example, certain diseases cause the dilation of the heart valve annulus. Dilation may also cause deformation of the valve geometry or shape displacing one or more of the valve cusps from the center of the valve. Other diseases or natural heart valve defects result in deformation of the valve annulus with little or no dilation.

Dilation and/or deformation result in the displacement of the cusps away from the center of the valve. This results in an ineffective closure of the valve during ventricular contraction, which results in the regurgitation or leakage of blood during ventricle contraction. For example, diseases such as rheumatic fever or bacterial inflammations of the heart tissue can cause distortion or dilation of the valvular annulus. Other diseases or malformations result in the distortion of the cusps, which will also lead to ineffective closure of the valve.

One method of repairing an impaired valve is to completely replace the valve. This method is particularly suitable for replacing a heart valve when one of the cusps has been severely damaged or deformed. While the replacement of the entire valve eliminates the immediate problem associated with a dilated valve annulus, presently available heart valves do not possess the same durability as natural heart valves. Various surgical procedures have been developed to correct the deformation of the valve annulus and retain the intact natural heart valve.

These surgical techniques involve repairing the shape of the dilated or elongated valve. Such techniques, generally known as annuloplasty, require surgically restricting the valve annulus to minimize dilation. Typically, a prosthesis is sutured about the base of the valve leaflets to reshape the valve annulus and restrict the movement of the valve annulus during the opening and closing of the valve.

A suitable prosthesis should allow the surgeon to properly reconstruct the heart valve annulus and minimize dilation, while allowing natural movement of the valve annulus during the opening and closing of the valve. The ability of the prosthesis to allow for a natural opening and closing of the valve is particularly important since such prostheses are not normally removed from the heart valve, even if the valve annulus heals to a normal geometry.

Many different types of prostheses have been developed for use in annuloplasty surgery. In general prostheses are annular or partially annular shaped members which fit about the base of the valve annulus. Initially the prostheses were designed as rigid frame members, to correct the dilation and reshape the valve annulus to the natural state. These annular prostheses were formed from a metallic or other rigid material, which flexes little, if at all, during the normal opening and closing of the valve.

Examples of rigid annuloplasty ring prostheses are disclosed in U.S. Pat. Nos. 3,656,185, issued to Carpentier on Apr. 18, 1972; and 4,164,046, issued to Cooley on Aug. 14, 1979. Certain artificial heart valves have also been developed with rigid frame members similar to the rigidity of the described valve prosthesis. Examples of this type of heart valve are disclosed in U.S. Pat. Nos. 4,204,283, issued to Bellhouse et al on May 27, 1980; and 4,306,319, issued to Kaster on Dec. 22, 1981.

Rigid annuloplasty ring prostheses adequately promote the healing of the valve annulus by restricting valve dilation and reshaping the valve annulus. However, this rigidity prevents the normal flexibility of the valve annulus. That is, a normal heart valve annulus continuously flexes during the cardiac cycle, and a rigid ring prosthesis interferes with this movement. Since the prosthesis remains implanted, even after the valve annulus has healed, a prosthesis of high rigidity will permanently restrict the normal opening and closing of the valve, and thus impair the normal functioning of the valve. Another disadvantage with a highly rigid ring prosthesis is the tendency of the sutures tearing during the normal movement of the valve annulus.

Other workers have suggested the use of completely flexible annuloplasty ring prostheses. Flexible prostheses include an inner support member formed from a flexible material. This support member is wrapped in woven, biocompatible cloth material. Resistance to the dilation of the annulus during the opening and closing of the valve is obtained by the proper suturing of the ring about the valve annulus.

One disadvantage with completely flexible ring prostheses is that during the implantation process the material forming the ring may become bunched at localized areas. This bunching of the prosthesis results in the phenomenon known as multiple plications of the ring prosthesis. One result of this phenomenon is variability of the ability of the ring to control the shape of the valve annulus. The bunched up areas of the ring tend to provide a more rigid area in comparison to the other portions of the ring which results in distorting the valve annulus during the opening and closing of the valve.

Examples of completely flexible ring prostheses are disclose in U.S. Pat. No. 4,290,151, issued to Massana on Sept. 22, 1981, and are discussed in the articles of Carlos D. Duran and Jose Luis M. Ubago, "Clinical and Hemodymanic Performance of a Totally Flexible Prosthetic Ring for Atrioventricular Valve Reconstruction", 5 Annals of Thoracic Surgery, (No. 5), 458-463, (Nov. 1976) and M. Puig Massana et al, "Conservative Surgery of the Mitral Valve Annuloplasty on a New Adjustable Ring", Cardiovascular Surgery 1980, 30-37, (1981).

Still further types of annuloplasty ring prostheses are designed to allow for adjustment of the ring circumference, either during the surgical implantation, or as the ring prosthesis during the opening and closing of the valve. This type of adjustable prosthesis is typically designed in combination with a rigid, or at least partially rigid frame member.

An example of a self adjusting ring prosthesis is taught in U.S. Pat. No. 4,489,446, issued to Reed on Dec. 25, 1984. This annuloplasty ring prosthesis provides for self adjustment of the prosthesis annulus by two reciprocating pieces which form the prosthesis frame. The basic disadvantage of this ring prosthesis is that the individual frame members are formed from a rigid material, with the resulting prosthesis suffering the same disadvantages discussed above for rigid ring prosthesis in general.

Other examples of adjustable ring prostheses are taught in U.S. Pat. Nos. 4,602,911, issued to Ahmadi et al and 4,042,979, issued to Angell on Aug. 23, 1977, provide for mechanism of adjusting the ring circumference. In Ahmadi et al the ring prosthesis frame is a coiled spring ribbon which is adjusted by a mechanical screw assembly. In Angell, a drawstring is used to adjust the circumference of a rigid frame member. Again, these ring prostheses suffer from the disadvantages of the rigid ring prosthesis discussed above. The Angell prosthesis could also possess a substantially flexible portion after suturing which could include multiple plications for the reasons discussed above for the completely flexible prosthesis.

U.S. Pat. No. 4,055,861, issued to Carpentier on Nov. 1, 1977 teaches an annuloplasty ring prosthesis which has a flexibility between the completely flexible rings discussed above and rigid ring. The ring of Carpentier is deformable to an equal degree and simultaneously in all directions. The preferred support is described as having the elasticity of an annular bundle of 2 to 8 turns of a cylindrical bristle of poly(ethylene terephthalate).

While rigid and semi-rigid annuloplasty rings provide a benefit over flexible rings, the restrictive nature of such rings may be detrimental to the ability of the valve to normally open and close. It thus remains an object to provide a flexible annuloplasty ring which does not have the any of the above described detriments.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 1 is a prospective exploded view of a annuloplasty ring prosthesis and holder assembly in accordance with an embodiment of the invention;

FIG. 2 is an exploded view of the ring mount portion and lower part of the handle portion of the holder assembly of FIG. 1;

FIG. 8 is a side prospective sectional view of a handle assembly is accordance with another embodiment of the invention;

FIG. 9 is a top view of the housing of FIG. 8; and

FIG. 10 is a bottom view of the handle extension of FIG. 8.

SUMMARY OF THE INVENTION

Figure 7:
FIG. 7 is a side view of an annuloplasty ring prothesis in accordance with a preferred embodiment of the invention.

The present invention overcomes the above discussed disadvantages by providing an assembly for holding a substantially flexible annuloplasty ring in a substantially taut position for suturing about a valve annulus. The assembly includes a portion which is formed with a surface against which the annuloplasty ring is positioned and held in a shape substantially equivalent to at least a portion of the valve annulus. The assembly further includes a mechanism for releasably binding the annuloplasty ring this surface.

The annuloplasty ring prosthesis used with the assembly of the invention is a generally elongated flexible body element formed from an internal flexible frame wrapped in a woven cloth material. Preferably, the annuloplasty ring prothesis has a lenticular or biconvex shape to reduce hemolysis caused by the shearing forces of blood passing around the ring.

The holder assembly includes a body which is formed with an outwardly facing surface against which is positioned the annuloplasty ring. This surface is dimensioned with a shape substantially similar to at least a portion of valve annulus. Preferably, this surface is formed with at least one depression for receiving a portion of the ring prosthesis.

A preferred version of the holder assembly includes a detachable handle. The detachable handle may be removed by the surgeon during the suturing procedure to allow for easier visibility of the ring during the suturing procedure. The lanyard ensures that the remaining portion of the holder assembly is easily withdrawn after the suturing procedure, and reduces the possibility of the surgeon leaving the remainder of the holder assembly in the patient.

The annuloplasty ring prosthesis is releasably retained against the body surface by at least a first thread. This thread is stitched through respective ends of the ring prosthesis and tied off to the body. The thread is tied off to the body to expose a portion which when can be cut to release the annuloplasty ring prosthesis from the body.

DESCRIPTION OF THE PREFERRED EMBODIMENTS

The present invention is directed to a holder assembly for holding a substantially flexible annuloplasty ring in a substantially taut position for suturing about a valve annulus. The prosthesis of the invention is formed from a flexible body about which a woven cloth is wrapped to form a covering. The annuloplasty ring prosthesis of the invention is surgically sutured, with the aid of the holder assembly, to the annulus of a dilated and/or deformed heart valve. The dilation and/or deformation of heart valves may be the result of a disease, natural defect or physical damage to the valve annulus. This dilated and/or deformed heart valve will not completely close, allowing for regurgitation of blood with a closed valve.

The suturing of the prosthesis to the valve annulus restricts the circumference of the dilated valve to a more natural dimension. The prosthesis of the invention thus restrains dilation of the valve and allows the surgeon to reshape the valve.

The holder assembly includes a ring mount assembly about which the annuloplasty ring is mounted and releasably affixed. Generally the ring mount assembly includes a ring support which formed with a shape similar to that of the valve annulus about which the annuloplasty ring is to be implanted. In one embodiment the ring mount assembly is a generally semi-circular or crescent shaped body. The annuloplasty ring prosthesis is fixed in position about this body in a taut relationship by piercing the respective ends of the annuloplasty ring with a suture or similar type filamenteous material, and drawing this suture tight. The annuloplasty ring prosthesis is released by cutting the suture.

Referring now to FIG. 1, an exploded view of a holder assembly to which an annuloplasty ring is mounted, as seen generally at 12 and 10 respectively. The holder assembly 12 includes a ring mount assembly 18 and handle assembly 40, which is formed from a handle 42 and housing 44.

Figure 4:
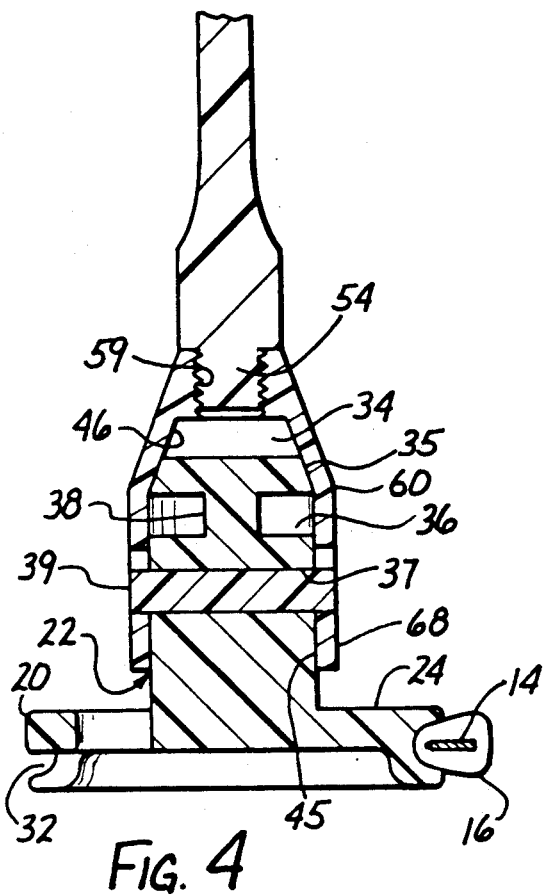
FIG. 4 is a cross sectional view of the assembled ring mount and lower handle portions of FIG. 3 along line 4—4.
Figure 3:
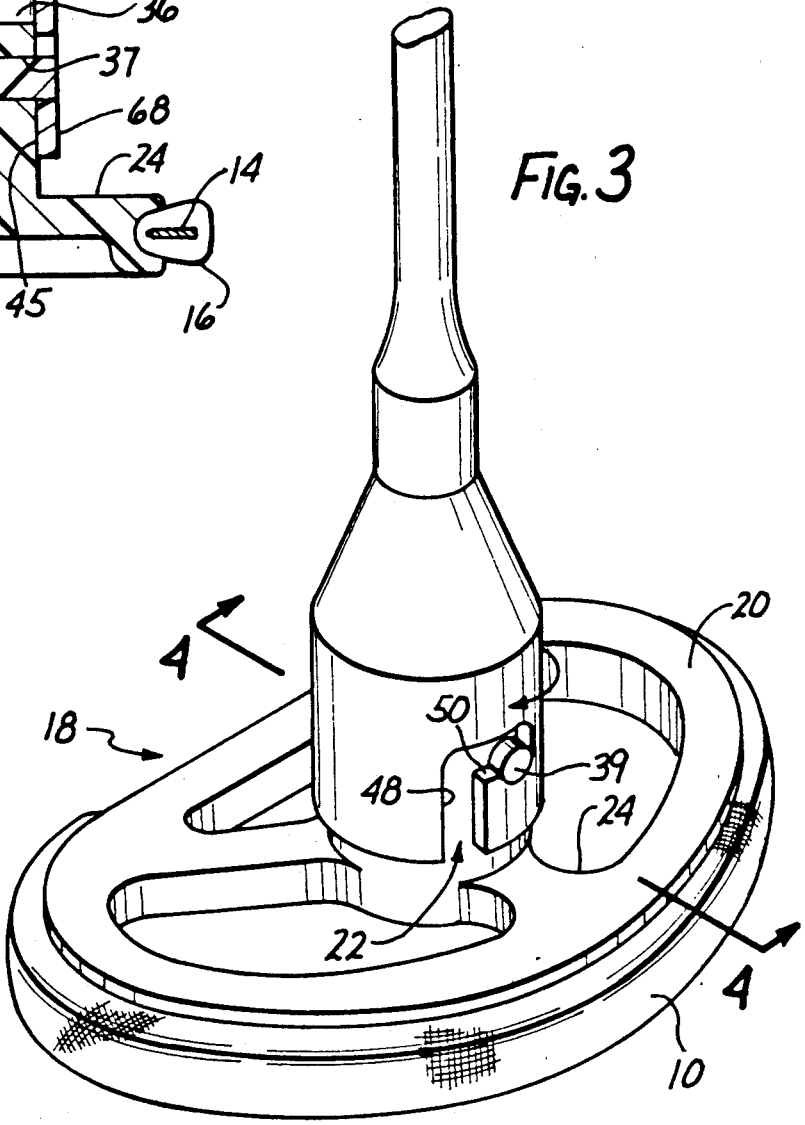
FIG. 3 is a prospective view of the assembled ring mount and lower handle portions seen in FIG. 2.
Figure 5:
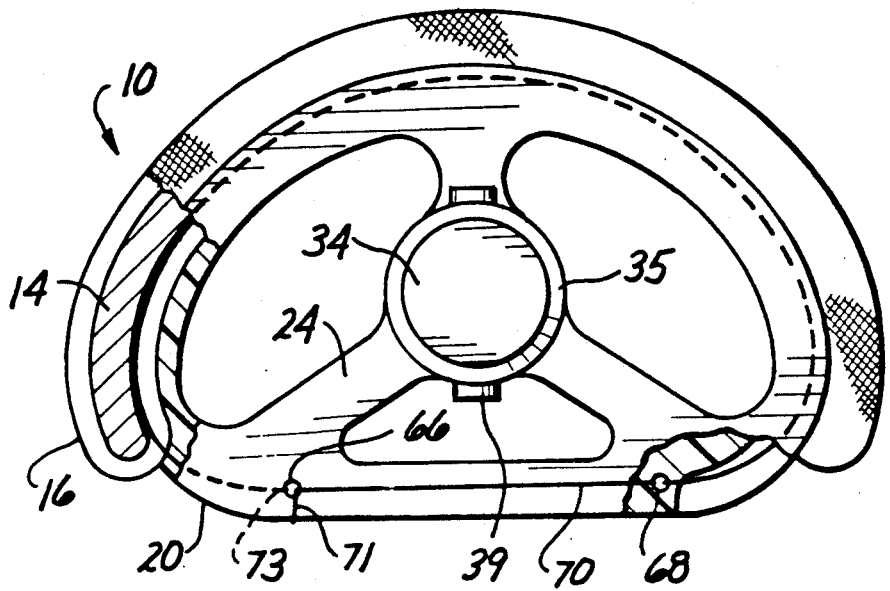
FIG. 5 is a top view of the ring mount seen in FIGS. 2-4 with a flexible annuloplasty secured thereto.

The annuloplasty ring prosthesis 10 is a generally straight member formed with an inner frame 14 about which is wrapped an outer cloth 16, as better seen in FIGS. 4 and 5. Frame 14 is formed from a flat or tubular piece of resilient, flexible material, e.g. MYLAR, with the outer cloth 16 formed from any biocompatible, woven cloth material is adequate for use as the outer cloth 16. Preferably, the outer cloth 16 is DACRON. This outer cloth 16 is tightly wrapped and sewn about this frame 14. The thickness of the outer cloth 16 is sufficient to allow the surgeon to pass a suture therethrough.

In accordance with a preferred embodiment, the annuloplasty ring prosthesis 10 is shaped to minimize the shearing action of blood passing over the ring. The preferred annuloplasty ring prosthesis 10 is lenticular or bi-convex in shape, as seen in FIG. 7. The lenticular shape of the ring 10 reduces the shearing action of the blood passing around the ring 10, thus limiting hemolysis. It is also preferable to reduce the overall height of the ring 10 to further minimize shearing action on the blood.

As seen in FIGS. 2 through 5, the ring prosthesis 10 is mounted about the lower portion of the holder assembly 12. This portion of the holder assembly 12 is the ring mount assembly 18. Ring mount assembly 18 includes a ring support 20. This ring support 20 is generally annular, with a shape similar to that of the annulus of the valve to which the ring prosthesis 10 is being sutured. More particularly, ring support 20 has a C-shaped portion 2B, with its ends connected by a straight side 30.

The ring prosthesis 10 is fitted about the curved C-shaped portion 2B of the ring support 20. The ring support 20 is formed with a groove or trough 32 which is dimensioned to receive a portion of the ring prosthesis 10, as best seen in FIG. 4. The positioning of the ring prosthesis 10 within the trough 32 slightly deforms the ring prosthesis 10. This deformation places a thicker portion of the woven cloth 16 outside of the trough 32 to allow the surgeon to pass a suture therethrough.

The ring mount assembly 18 also includes a central support hub 22 to which the ring support 20 is attached by three integrally formed spokes, one of which is seen at 24. The arrangement allows the surgeon to visual observe the heart valve during the suturing process. Central support hub 22 is formed with an annular groove 36. This groove 36 is formed proximate that end 34 of hub 22 opposite ring support 20, and defines a post member 3B. That portion of hub 22 remaining at that side of the groove 36 opposite the ring support 20, hub end 34, includes an inwardly tapering peripheral surface, as seen generally at 35. The hub 22 is also includes an open bore 37 through which is fitted a cylindrical plug 39. The plug 39 is dimensioned to extend out from both sides of the bore 37. The purpose of tapered surface 35, and the plug 39 will be described in greater detail herein.

As stated the handle assembly 40 includes an elongated post 42 and a housing 44. As seen in FIG. 1, housing 44 is mounted to an end 54 of post 42. While the housing 44 may be integrally formed at the end 54 of the post 42, preferably end 54 is formed with outwardly facing threads. These threads are formed to threadably mate with threads formed along a surface of an opening formed in the top of the housing 44, seen generally at 59. The opposite end of the post 42 is formed with an external etched surface 52. This etched surface 52 assists the surgeon in gripping post 42.

Housing 44 is a thimble shaped structure having a circular wall 60 which defines a cavity 46. As seen better in FIG. 4, cavity 46 is open at one side, seen generally as opening 45. The inner surface of the circular wall 60 inwardly converges a short distance from the opening 45. The cavity 46 is generally wide enough at the open side 45 to snuggly receive hub 22, but the plug 39 extends sufficiently outward from hub 22 to prevent passage through open side 45 into cavity 46. Wall 60 is formed with two J-shaped notches, seen at 4B and 49 in FIGS. 2 and 3. These J-shaped notches 48 and 49 are formed and positioned to respectively receive the ends of the plug 39 extending outward from the hub 22. The shape of the notches 48 and 49 defines a landing 50 between the long and short legs of each notch.

Handle assembly 40 is coupled to the ring mount assembly 18 by inserting end 54 of the hub 22 into the cavity 46, with the outwardly extending ends of the plug 39 passing through a respective on of each J-shaped notch 48 and 49. The tapered surface 35 of the hub 22 engages the inwardly tapering surface of the wall 60. This causes a slight compression of the hub end 34, resulting in a spring force. The spring force acts to restrain the movement of the outwardly extending ends of the plug 39 through the larger legs of the J-shaped notches 48 and 49. Additional exertion moves the plug 39 ends through the larger legs of J-shaped notches 48 and 49, with rotation of the handle 40 passing the outward ends of the plug 39 across the landings 50 and into the smaller leg of each J-shaped notch 48 and 49.

The spring force established by the slight compression of the hub end 54 maintains the assembly of the housing 44 and ring mount assembly 18. The handle 40 is decoupled from the ring mount assembly 18 by reversing the described procedure.

The mechanism for attaching the ring prosthesis 10 to the ring support 20 of the ring mount assembly 18 is seen in FIG. 5. Ring support 20 is formed with two holes 66 and 68. Each of the holes 66 and 68 is formed through the ring support 20 and communicates with the groove 32. The exact positioning of the holes 66 and 68 is not critical. As illustrated these holes 66 and 68 are formed along the straight portion of the ring support 20, at a location proximate two of the spokes 24.

One end 71 of a cord or suture 70 is passed through one of the holes, as illustrated hole 66, and tied off on the ring support 20. The other end 73 of suture 70 is passed through the body of ring prosthesis 10 from one end to the other. This end 73 is then passed first through hole 68 and then through and tied off at hole 66. After the ring prosthesis 10 is sutured in position about the valve annulus, that portion of the suture 70 between the two holes 66 and 68 is sniped. The suture 70 passes out of the ring prosthesis 10 by withdrawing the handle assembly 12.

In accordance with another embodiment, the first end 71 is tied off at hole 66, with the second end 73 passed first through one end of the ring prosthesis 10, and then brought back across and passed through the other prosthesis 10 end. This suture end 73 is again tied off at hole 66. Removal of suture 70 is accomplished by sniping the suture between the two holes.

Figure 6:
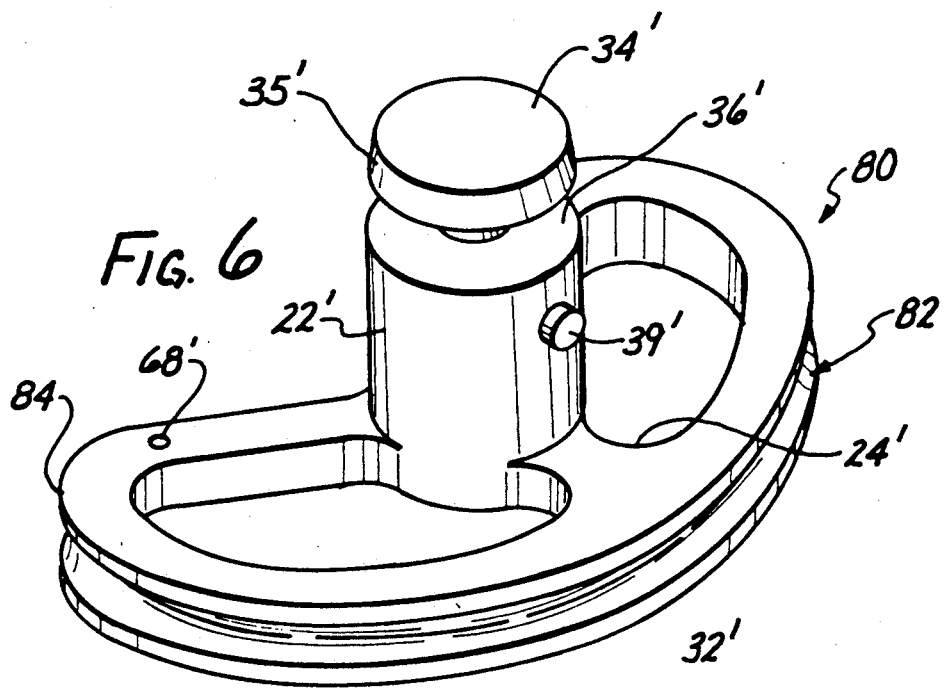
FIG. 6 is a prospective view of a ring mount in accordance with another embodiment of the invention.

The above described ring mount assembly 18 includes a ring support 20 formed by a C-shaped and straight side as best seen in FIG. 5. A second embodiment is seen in FIG. 6. This ring mount assembly 80 includes a ring support 82 which is formed with only an open C-shaped side 84. Except for the stated difference in shape of the ring support 82, this ring mount assembly 80 includes similar elements as those described for ring support 20, which are indicated by the prime of the previously provided element number, and will not be described in any more detail herein. This embodiment of ring mount assembly 80 provides an open area across which a suture is positioned after being tied off at the respective hole 66.

In a preferred embodiment of the invention, the handle assembly 40 is tethered to the ring mount assembly 18. As seen in FIG. 1, this tethering is performed by connecting one end of a lanyard, seen generally at 100, to the handle assembly 40 and the other end of the lanyard 100 to one of the spokes 24. The lanyard 100 allows a surgeon to detach the handle assembly 40 from the ring support 20 during the suturing procedure. This would allow a clearer view of the annuloplasty ring 10. The tethering of the assembly handle 40 to the ring mount assembly 18 reduces the risk of the surgeon leaving the ring support 20 in the patient after completion of the procedure. The lanyard 100 also allows the surgeon to easily remove the ring support 20 after the handle has been detached.

In a still further preferred embodiment, a handle assembly is modified to house a spool of suture or string. The string is attached at opposite ends to the handle assembly and the ring mount assembly respectively. This string spools out of the handle assembly after disconnection from the ring mount assembly.

This preferred embodiment is better seen in the several FIGS. 8 through 10. The lower portion of a handle assembly in accordance with this embodiment is better seen in FIG. 8 at 90. Handle assembly 90 includes a housing 92, a handle extension 94 and a handle post 96. Housing 92 includes a pair of opposing J-shaped notches 98 and 99 which function similarly to the J-shaped notches 48 and 49 described above. The handle extension 94 is fastened to the lower end of the handle post 96 in any suitable manner. As shown the handle extension 94 includes at one a bore 102 for receiving the lower end 104 of the handle post 96. The handle port end 104 may be held in bore 102 by welding, stamping or by providing the respective members with interlocking threaded surfaces. Accordingly, neither of these structures of the handle assembly 90 will be discussed in any greater detail.

The main distinction to the previously described embodiment is that the handle assembly 90 is formed to carry a spool of suture, seen generally at 106. This suture spool 106 is housed in a bore 112 formed in the handle extension 94. The handle extension 94 and housing 92 are formed to releasably fit together. The handle extension 94 and housing 92 include mating collars 108 and 110, respectively. Collar 108 is formed with a groove 114 which receives a tongue 116 extending upward from the collar 110. Tongue 116 is formed with a central aperture 122, and two opposing cut-aways 118 and 120 which extend out in opposite directions from this aperture 122.

Each of the collars 108 and 110 possess four apertures, apertures 126-129 of handle extension 94, and apertures 130-133 which are aligned when the handle extension 94 and housing 92 are fitted together.

The suture spool 106 is formed by winding a length of suture into a cylindrical configuration which is fitted into the bore 112. The opposite ends of this suture length are tied to the tongue 116 and the handle extension 94. One end of the suture is drawn through the central aperture 122 and tied to the tongue 116, as seen at 115. The opposite end of the suture is drawn through an opening 124 extending from the bore 112 through the handle extension 94 and tied around the handle extension 94, as seen at 117. It should be noted that for the purpose of this invention "suture" shall mean to include any cord, string or filamentous material useful for tethering the housing 92 to the handle extension 94.

The handle extension 94 and housing 92 are fitted together by placing the tongue 116 into the grove 114. Sutures are run through aligned apertures to hold the handle extension 94 and housing 92 together. For example, one suture 134 is passed through apertures 126 and 127 of handle extension 94 and apertures 130 and 131 of housing 92, while a second suture 136 is passed through apertures 128 and 129 of handle extension 94 and apertures 132 and 133 of housing 92.

The handle assembly 90 of this embodiment is coupled to the ring mount assembly 18 as stated above. The handle post 96 is removed from the housing 92 by cutting the sutures 134 and 136 and pulling the handle extension 94 away from the housing 92. The pulling away of the handle post 96 unravels the suture spool 106. After the ring prosthesis is sutured in position about the heart valve the suture holding the ring mount assembly to the prosthesis is cut. The ring mount assembly is removed by pulling on the handle post 96.

While the preferred embodiments have been described, various modifications and substitutions may be made thereto without departing from the scope of the invention. Accordingly, it is to be understood that the invention has been described by way of illustration and not limitation.

What is claimed is:

1. An annuloplasty ring assembly comprising: a substantially flexible annuloplasty ring;

a body defining a semi-circular shaped surface against which said annuloplasty ring is positioned;

means for tautly and releasably retaining said annuloplasty ring prosthesis against said semi-circular shaped surface;

a handle detachably coupled to said body; and means for tethering said handle to said body.

2. The annuloplasty ring assembly of claim 1 wherein said tethering means comprises:

a spool of a length of filamenteous material tied at one end to said body and at an opposite end to said handle, which spool is held within a cavity of said body.

3. The annuloplasty ring assembly of claim 2 wherein said releasable and tautly retaining means is a filamenteous material selectively passed through said annuloplasty ring prosthesis and tied to said body.

4. The annuloplasty ring assembly of claim 3 wherein said body defines a groove into which said ring partially fits, said body further having at least one aperture through which said filamenteous material is tied to said body.

5. The annuloplasty ring assembly of claim 4 wherein said filamenteous material has two opposite ends respectively stitched through said ring, which ends are also tied off to said body.

6. The annuloplasty ring assembly of claim 1 wherein said tethering means comprises a length of filamenteous material tied at one end to said body and at an opposite end to said handle.

7. An annuloplasty ring and holder assembly combination comprising:

a substantially flexible annuloplasty ring;

a holder means for holding said annuloplasty ring in a substantially taut position for suturing about a valve annulus, said holder means including a body formed with a surface for receiving said annuloplasty ring;

a handle releasably coupled to said holder means;

tethering means for interconnecting said holder means and said handle after release of said handle from said holder means; and a releasable retaining means for selective attachment to said annuloplasty ring and said holder means, said releasable retaining means being operable to release said annuloplasty ring while maintaining attachment to said holder means.

8. The combination of claim 7 wherein said releasable retaining means is at least a first thread having two opposing ends selectively attached to said holder means body and said annuloplasty ring.

9. An assembly useful for holding a substantially flexible annuloplasty ring in a substantially taut position for suturing about a valve annulus comprising:

holder means including a body formed with a surface for receiving said annuloplasty ring;

a handle releasably coupled to said holder means;

tethering means for interconnecting said holder means and said handle after release of said handle from said holder means; and releasable retaining means for selective attachment to said annuloplasty ring and said holder means, said releasable retaining means being operable to release said annuloplasty ring while maintaining attachment to said holder means, said releasable retaining means includes at least a first thread having opposing ends, at least a portion of said first thread adapted for passing through a portion of said annuloplasty ring, with both of said thread ends being affixed to said holder means body to expose a portion of said thread which when cut allows said thread to be freely withdrawn, in one or more segments, from said annuloplasty ring while remaining attached to said holder means body.

* * * * *